United States Patent [19]

Weijland

[11] Patent Number: 5,319,398
[45] Date of Patent: Jun. 7, 1994

[54] METHOD OF AND APPARATUS FOR TESTING VISUAL FUNCTIONS OF HUMAN EYES

[75] Inventor: Albert Weijland, Wetzikon, Switzerland

[73] Assignee: Interzeag AG, Schlieren, Switzerland

[21] Appl. No.: 824,789

[22] Filed: Jan. 16, 1992

[30] Foreign Application Priority Data

Jan. 18, 1991 [CH] Switzerland .................... 140/91

[51] Int. Cl.⁵ .............................................. A61B 3/10
[52] U.S. Cl. ................................. 351/212; 351/211; 351/246
[58] Field of Search ............... 351/246, 212, 206, 224, 351/211

[56] References Cited

U.S. PATENT DOCUMENTS

| | | | |
|---|---|---|---|
| 3,883,235 | 5/1975 | Lynn et al. | 351/246 |
| 4,012,128 | 3/1977 | Regan. | |
| 4,083,365 | 4/1978 | Yancey. | |
| 4,429,961 | 2/1984 | Sheingorn | 351/224 |
| 5,046,835 | 9/1991 | Billeter | 351/206 |

FOREIGN PATENT DOCUMENTS

0320767 12/1988 European Pat. Off. .
0363610 8/1989 European Pat. Off. .

Primary Examiner—William L. Sikes
Assistant Examiner—Hung Xuan Dang
Attorney, Agent, or Firm—Darby & Darby

[57] ABSTRACT

A computerized perimeter is utilized to examine the field of vision of a subject's eye while the eye is located at or at least close to a predetermined position in which the optical axis of the eye is maintained in or at least close to a predetermined orientation. The eye is presented with a sequence of stimuli which issue from a radiation source and are transmitted, as a rule only once, to each of a plurality of computer-selected locations in the area of the optical of the eye at the predetermined position. The value (the intensity and/or the size) of each stimulus is increased until the eye discerns the presented stimulus and the subject reacts as a result of discernment of the presented stimulus. Subjective and/or objective signals are generated by the subject in response to detection of stimuli, i.e., each such signal can be said to denote that value of a stimulus which is sufficiently high to ensure discernment of the stimulus by the eye. Such signals are transmitted to the computer and the computer utilizes the signals to terminate the presentation of a stimulus in response to reception of the corresponding signal.

17 Claims, 2 Drawing Sheets

METHOD OF AND APPARATUS FOR TESTING VISUAL FUNCTIONS OF HUMAN EYES

CROSS-REFERENCE TO RELATED CASE

The apparatus for the practice of my improved method is somewhat similar to those which are described and shown in commonly owned U.S. Pat. No. 5,046,835 granted Sep. 10, 1991 to Ernst Billeter et al. for "Apparatus for testing visual functions of human eyes". The disclosure of the patent to Billeter et al. is incorporated herein by reference.

BACKGROUND OF THE INVENTION

The invention relates to improvements in methods of and apparatus for testing visual functions of human eyes, and more particularly to improvements in methods of and apparatus which employ perimeters.

Perimetric examination of a subject's eye involves the determination of sharpness of visual perception on the retina. To this end, and as disclosed in the patent to Billeter et al., the eye to be examined is maintained in a predetermined position and the permeter presents to the eye a plurality of stimuli at a plurality of selected locations in the area of the optical axis of the eye to be examined. The various locations can constitute a raster in a plane which is normal to the optical axis of the eye. The perimeter presents to the eye stimuli of predetermined value (intensity), and the patient acknowledges the detection or discernment of a stimulus by actuating a knob or a like device. The test is thereupon repeated with a sequence of stimuli having different values; such stimuli can be presented to the eye at each of the predetermined locations which were selected for the first test or at a selected number of such predetermined locations. The second test is followed by a third test which presents to the eye stimuli having a third value, and so forth. The testing operation is terminated when the perimeter or the person in charge ascertains (either empirically or by calculation) a series of threshold values of stimuli which are discerned by the eye of the subject at the selected locations in the aforementioned plane that crosses the optical axis of the eye.

A drawback of the aforedescribed conventional methods and apparatus is that the completion of each test takes up a substantial amount of time. Moreover, the examination is tiresome to the subject because the subject must cause the initiation of each and every signal to indicate whether or not a stimulus of a particular value has been perceived by the eye under test. The reliability of a subject's reaction decreases as the testing operation proceeds so that the final results of the examination are often misleading.

In order to shorten successive tests or stages of a complete examination and to thus enhance the accuracy of the examination, it is already known to correct previously gathered and stored information pertaining to the perception of stimuli at some or all of the aforediscussed locations in the area of the optical axis of the eye which is being tested. The correction involves modifying the previously obtained threshold values in dependency on the more recently ascertained threshold values and storing the thus modified threshold values of stimuli for utilization in the course of a later examination of the same eye. Such examination at a later time can include presenting to the eye stimuli of a value corresponding to the previously ascertained and stored threshold values for some or all of the locations. It has been found that such improved method also exhibits a number of drawbacks, particularly as concerns the duration of an examination. Thus, it is still necessary to present a plurality of stimuli having different values at least to a plurality of different locations in the area of the optical axis of the eye which is being tested. The new threshold value for each test location must be ascertained by bracketing in a number of successive stages comprising visible and invisible stimuli which prolongs the examination and is tiresome to the subject in addition to adversely influencing the accuracy of the tests. The just outlined method involves applying to each of several different portions of the retina a plurality of stimuli in order to ascertain a stimulus just below the limit of perception and a stimulus just above such limit. These stimuli are thereupon averaged to ascertain the median value or another mathematical function of the two stimuli. Such procedure is called bracketing the sought-after average value of stimuli for a particular part of the retina, i.e., bracketing renders is possible to ascertain, in accordance with heretofore known methods, a series of stimuli—each for a different part of the retina—each of which is somewhere between a still imperceptible stimulus and a barely perceptible stimulus.

OBJECTS OF THE INVENTION

An object of the invention is to provide a novel and improved method of examining the field of vision of a subject's eye within an interval of time which is a small or minute fraction of the intervals which elapse for carrying out heretofore known methods.

Another object of the invention is to provide a method which is less strenuous to the subject than a conventional method and which renders it possible to carry out the examination with a heretofore unknown degree of accuracy.

A further object of the invention is to provide a method which need not involve an examination in a plurality of successive stages.

An additional object of the invention is to provide a method which renders it possible to avoid subjective determination of perception of a stimulus by the subject.

Still another object of the invention is to provide a method which can be carried out by resorting to relatively simple and compact apparatus.

A further object of the invention is to provide a method which involves or can involve a single presentation of a stimulus to each of a large or small number of various locations in the area of the optical axis of the eye of a subject.

Another object of the invention is to provide a novel and improved apparatus for the practice of the above outlined method.

An additional object of the invention is to provide the apparatus with novel and improved means for initiating the generation of signals denoting detection of stimuli by the eye of a subject.

A further object of the invention is to provide the apparatus with novel and improved means for varying the value of stimuli which are being presented to the eye of a patient or another subject.

Another object of the invention is to provide an apparatus which can employ numerous component parts of heretofore known apparatus.

A further object of the invention is to provide a novel and improved computerized perimeter.

SUMMARY OF THE INVENTION

One feature of the present invention resides in the provision of a method of examining the field of vision of a subject's eye with a computer-controlled perimeter. The improved method comprises the steps of locating the eye to be examined in the perimeter at (or at least close to) a predetermined position in which the optical axis of the eye is maintained in (or at least close to) a predetermined orientation, presenting to the eye in such position a sequence of stimuli from a source of radiation and—as a rule—only once at each of a plurality of computer-selected locations in the area of the optical axis of the eye, increasing the value of each stimulus until the eye discerns the presented stimulus and the subject reacts in one or more ways as a result of discernment or detection of the presented stimulus, generating signals denoting that value of each stimulus which is sufficiently high to ensure that the stimulus is discerned by the eye, transmitting such signals to the computer, and terminating the presentation of stimuli in response to transmission of corresponding signals to the computer.

The step of increasing the value of each stimulus can include continuously increasing the value or increasing the value in a plurality of steps or stages. Furthermore, the step of increasing the value of each stimulus can include increasing the intensity of radiation from the source and/or increasing the size (area) of each stimulus.

The step of generating signals can include subjective generation of signals by the subject, e.g., actuation by the subject of a signal generating knob or an analogous device upon discernment or detection of a stimulus.

Alternatively, the step of generating signals can include objective generation of signals by the subject. For example, such objective generation can include monitoring the pupil of the eye at the aforementioned position and generating signals in response to those changes of the pupil which are indicative of discernment or detection of stimuli by the eye. The monitoring step can include observing the eye at the predetermined location with a CCD camera which is sensitive to infrared light. If desired, objective generation of signals by the subject can include monitoring a part of the subject other than the eye at the predetermined position to ascertain changes of voltage as a result of increasing value of stimuli, and generating signals in response to detection of voltages which are indicative of discernment or detection of the respective stimuli by the eye at the predetermined position. The monitoring can include monitoring the brain of the subject for changes of brain waves.

Another feature of the invention resides in the provision of an apparatus (preferably in the form of an automatic perimeter) for examining the field of vision of a subject's eye. The apparatus comprises a perimeter having means for locating the eye at (or at least close to) a predetermined position in which the optical axis of the eye is maintained in (or at least close to) a predetermined orientation, a source of radiation, and means—including a computer—for presenting to the eye at the predetermined position from the radiation source a sequence of stimuli of increasing value, as a rule only once at each of a plurality of computer-selected locations in the area of the optical axis of the eye at the predetermined position whereby the eye discerns or detects a stimulus of a particular value. The apparatus further comprises means for transmitting to the computer signals to terminate the presentation of a stimulus in response to detection of such stimulus by the eye at the predetermined position.

The means for presenting stimuli can include means for presenting stimuli of continuously increasing value or means for presenting stimuli of a value which increases in a plurality of stages or steps.

The signal transmitting means can include subject-operated signal transmitting means, e.g., a knob which is actuated by the subject in response to detection of a stimulus. Alternatively, the signal transmitting means can include objective signal transmitting means such as a camera which scans the pupil of the eye in the predetermined position and transmits to the computer a signal when the change of the pupil is indicative of detection of a stimulus, or a sensor which can generate signals in response to detection of voltages in a particular part of the subject (e.g., a sensor which monitors the brain waves of the subject).

The novel features which are considered as characteristic of the invention are set forth in particular in the appended claims. The improved method itself, however, together with additional features and advantages thereof, will be best understood upon perusal of the following detailed description of certain presently preferred specific embodiments with reference to the accompanying drawing.

DESCRIPTION OF PREFERRED EMBODIMENTS

Figure 1:
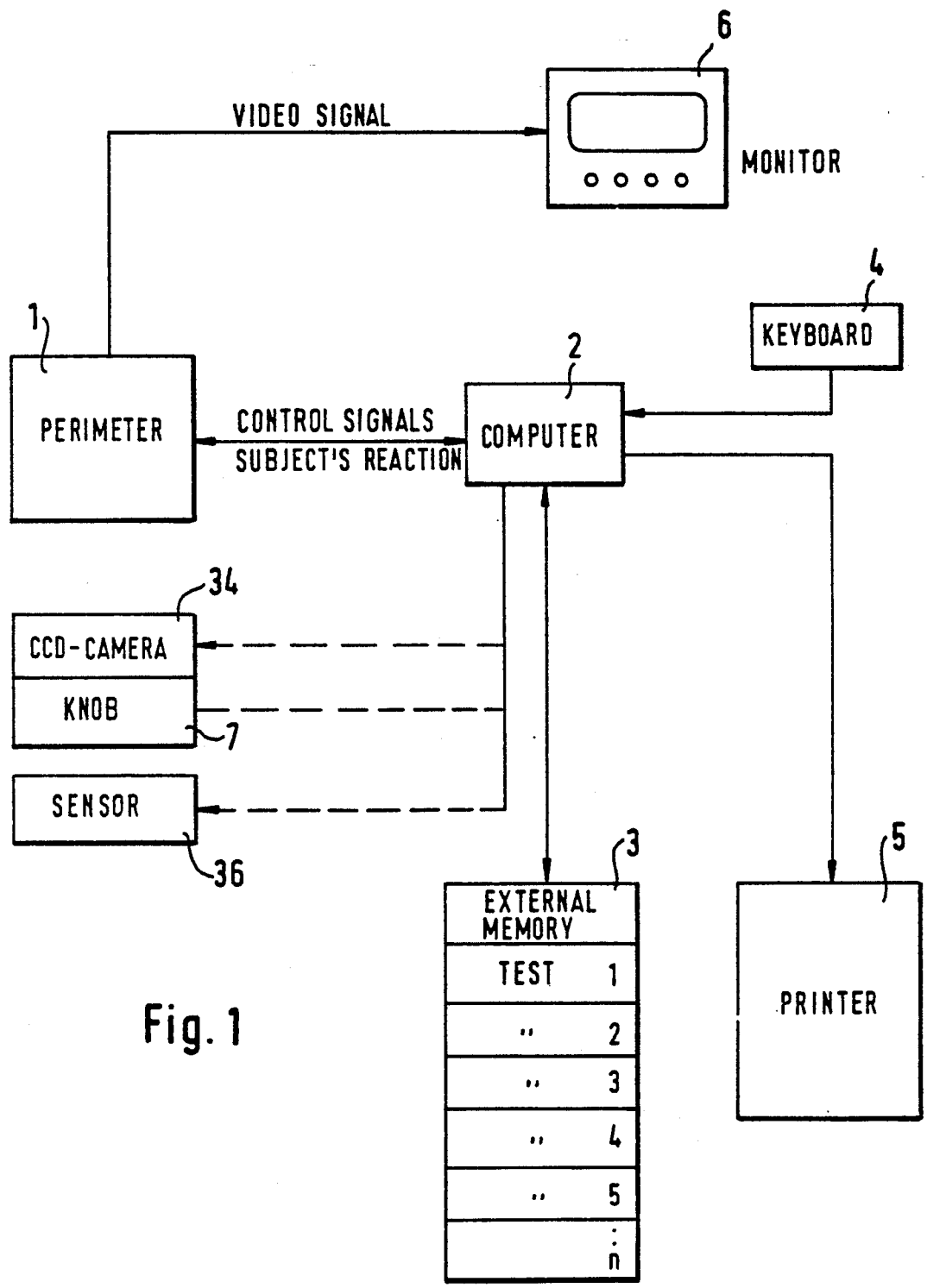
FIG. 1 is a diagrammatic view of an automatic perimeter which can be utilized for the practice of the improved method.

The apparatus which is shown in FIG. 1 constitutes an automatic perimeter. The actual perimeter 1 of this apparatus is connected with a computer 2 having an internal memory (not shown) and being connected with an optional external memory 3 for storage of information pertaining to a sequence (1 to n) of tests.

Figure 2:
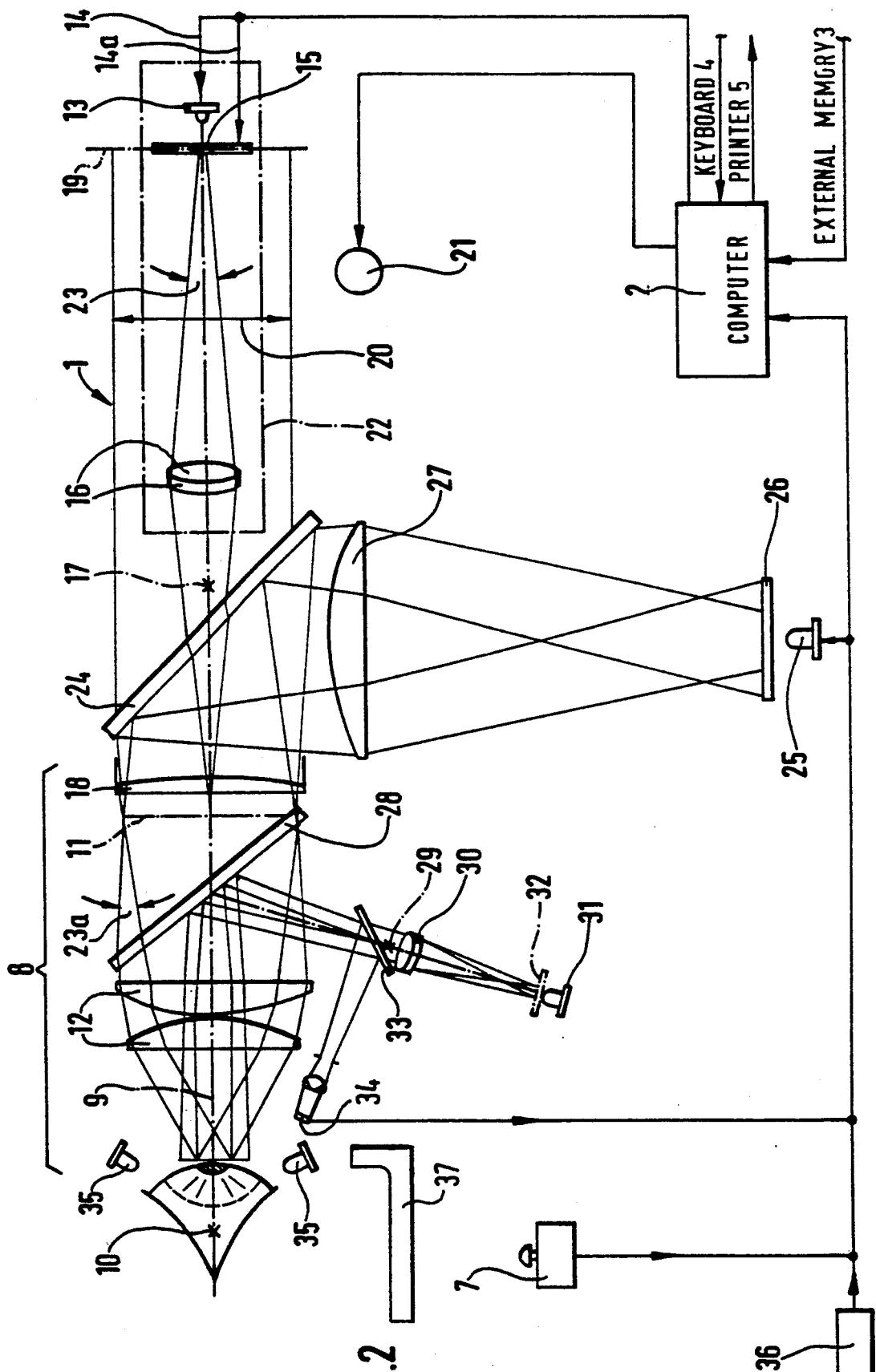
FIG. 2 is a more detailed diagrammatic view of the automatic perimeter of FIG. 1.

The perimeter 1 is shown in greater detail in FIG. 2 and comprises means (e.g., including a chin rest 37) for properly positioning a patient's or another subject's eye 10 for testing its visual functions. The connection between the perimeter 1 and the computer 2 serves for transmission of control signals from the computer and for transmission of signals denoting a subject's reaction to the computer. The eye 10 occupying the predetermined position of FIG. 2 is presented with stimuli of increasing value in an area surrounding the optical axis 9 of the lens of the eye 10. The information relating to a series of tests and being stored in the internal memory of the computer 2 and/or in the external memory 3 can pertain to ascertained threshold values of local sensitivity of different portions of the eye to the presented stimuli. The reference character 4 denotes in FIG. 1 a keyboard which can be said to constitute a source of control signals to be transmitted to the eye 10 in the position of FIG. 2.

An output of the computer 2 is connected with a printer 5 which serves to record the received numerical and/or graphical information, i.e., the printer 5 can record the information which is stored in the internal memory and/or in the external memory 3 of the computer 2. A monitor 6 is provided with a screen which displays information that can be evaluated to ascertain whether or not the optical axis of the lens of the eye 10 in the position of FIG. 2 coincides with the axis of an eyepiece 8 of the perimeter 1. The monitor 6 can establish communication between the eyes of the observer (person in charge) and the computer 2 via perimeter 1.

The combination of perimeter 1 and computer 2 generates for each test location (such test location is determined by the just mentioned combination) a stimulus the value of which increases continuously for each test location, or its value increases stepwise or in stages at timely spaced intervals. Thus, each stimulus can be said to constitute a ramp type (substantially linearly increasing) stimulus. The lowermost value of each stimulus is slightly below the threshold level, and its standard value is corrected in dependency on the age of the patient to be presented to the subject with an increasing light quantity until the stimulus is perceived by the eye 10. The quantity of light for each stimulus can be increased in the form of varying (increasing) intensity or in the form of a varying (increasing) size or area of the respective stimulus. This is determined by the computer 2.

The subject can react and transmit corresponding signals to the computer 2 in one or more different ways, e.g., by actuating a knob 7 which is connected to the corresponding input of the computer 2 and is shown in FIGS. 1 and 2. The computer 2 can transmit corresponding signals to the perimeter 1. Such subjective indication of detection or discernment of a stimulus by the subject herself or himself is known, for example, from the aforementioned commonly owned patent to Billeter et al. Thus, transmission of a recognition signal to the computer 2 awaits manual actuation of the knob 7. Alternatively, the knob 7 can be actuated when the subject fails to discern a stimulus; thus absence of a signal from the knob 7 then constitutes a signal denoting detection of a stimulus.

In addition to or in lieu of transmission of recognition signals via knob 7, the computer 2 can receive such recognition signals in an objective (automatic) manner as a result of a change of the pupil at the instant of subjective detection of a stimulus by the eye 10 of a subject. This is shown at 34 in FIGS. 1 and 2, i.e., the apparatus comprises an infrared light sensitive CCD camera which is trained upon the eye 10 and transmits to the computer 2 a signal as soon as the pupil changes as a result of detection of a stimulus by the eye 10 in the position of FIG. 2.

Thirdly, the apparatus can be equipped with a sensor 36 which is designed to detect the development and/or changes of a potential resulting from detection or discernment of a stimulus by the eye 10. For example, the sensor 36 can be properly connected to the head of a subject to register changes of brain waves and/or changes of potential which are caused by another part or organ of a subject's body as a result of detection of a stimulus by the eye 10 in the position of FIG. 2.

The heretofore described method and apparatus exhibit a number of important advantages. Thus, the tests can be completed within a small fraction (e.g., one-fifth) of the interval which is required for testing in accordance with heretofore known methods not involving the application of stimuli having a progressively or otherwise increasing value. Transmission of signals from the device including the camera 34 and/or the sensor 36 entails an objective determination that the subject has detected a stimulus, namely a determination which cannot be influenced (e.g., faked) by the subject because the devices 34, 36 can transmit signals which emanate from the subject but whose generation cannot be improperly influenced by the person undergoing a test. The method can be utilized for perimetric examination of the eyes of retarded, juvenile, senile and/or otherwise handicapped subjects. The tests are more reliable than those which are carried out in accordance with heretofore known methods.

FIG. 2 shows the details of a presently preferred apparatus which can be utilized for the practice of the above outlined improved method. Many constituents of this apparatus are similar to or identical with those shown in FIG. 2 of the patent to Billeter et al. as well as in the corresponding published European patent application No. 0 363 610.

The eyepiece 8 of the perimeter 1 which is shown in FIG. 2 has an optical axis which coincides with the optical axis 9 of the lens of a properly positioned and oriented eye 10 to be examined. The eyepiece 8 includes optical elements 12 and a field lens 18. The optical elements 12 are focussed upon a real image plane 11 (indicated by a dot-dash line) which is shown to be flat but can be slightly curved in actual practice, and the optical elements 12 are ground and/or otherwise finished so that they convert divergent beams of radiation which propagates itself beyond a selected point of the plane 11 into parallel rays and direct the parallel rays toward the eye 10 in the position of FIG. 2. It can be said that, with reference to the plane 11 of the real images of stimuli, the eyepiece 8 constitutes a magnifying lens system. An advantage of optical elements 12 and of parallel rays which propagate themselves from the elements 12 toward the eye 10 is that the eye can be shifted, within certain limits, transversely of the optical axis 9 without affecting the sharpness of stimuli and/or without preventing the subject from perceiving (or not perceiving at all) those stimuli which would have been perceived by an eye occupying the prescribed or optimal position shown in FIG. 2 and/or those stimuli whose geometrical position was improperly perceived by the eye.

The perimeter 1 further comprises a radiation source 13, preferably one or more light emitting diodes, which is connected to an output 14 of, and the radiation intensity of which can be regulated by, the computer 2. An advantage of a radiation source 13 which comprises one or more light emitting diodes is that the intensity of emitted radiation can be regulated without any delay. Moreover, one or more standard light emitting diodes can be readily replaced with one or more diodes for emission of colored light if the apparatus of FIG. 2 comprises means for carrying out color perimetric examinations. However, it is equally within the purview of the invention to provide a radiation source 13 which employs one or more halogen lamps or a source of laser beams.

The size of the aperture in a diaphragm 15 which is installed in front of the radiation source 13 determines the size or area and the shape of stimuli which are transmitted toward one or more collector lenses 16, i.e., toward a means for transmitting real images of stimuli into the plane 11. The aperture of the diaphragm 15 permits the passage of a beam of coherent light, and this diaphragm is located in the focal plane 19 (indicated by a phantom line) of the collector lenses 16. The diaphragm 15 is preferably adjustable, i.e., the size of its aperture can be varied in response to signals which are transmitted by a further output 14a of the computer 2.

The adjustability of the radiation source 13 as well as of the diaphragm 15 in response to signals from the computer 2 constitutes a desirable feature of the improved method, i.e., the value (intensity and/or size) of each stimulus can be increased in stages or steps or continuously (gradually).

As mentioned above, the plane 19 of the adjustable diaphragm 15 coincides with the focal plane of the collector lenses 16 which serve to transmit the real images of stimuli into the plane 11. The optical axis 17 of the collector lenses 16 is parallel with or coincides with the optical axis 9 of the eye 10 (in the position of FIG. 2) and the eyepiece 8. The enlarged real intermediate images of stimuli in the plane 11 are perceived by the eye 10 through the eyepiece 8 which includes the optical elements 12 and the field lens 18.

The radiation source 13 and the diaphragm 15 are movable, preferably as a unit, at right angles to the optical axes 9 and 17 by a computer-controlled drive 21. This renders it possible to shift the stimuli in the plane 19 to any one of a number of accurately determined locations (the exact coordinates of such locations are determined by the computer 2 via drive 21) so that the stimuli can be transmitted within the range of the collector lenses 16 in an area 20. The drive 21 further serves to shift the lenses 16 together with the diaphragm 15 and together with the radiation source 13. To this end, the parts 13, 15, 16 can be grouped into an assembly 22 (indicated by phantom lines) to be moved at right angles to the axis 17 in response to signals from the computer 2 to the drive 21. The latter can shift the entire assembly 22 as a unit to any one of a large number of locations to thereby shift the stimuli in the plane 19 of the diaphragm 15 in response to signals from the computer 2. Due to movability of the collector lenses 16, it is possible to select their diameters and hence the magnitude of the apex angle 23 of the cone of radiation which issues from the aperture of the diaphragm 15. Furthermore, it is possible to install the lenses 16 at a short distance from the plane 19 of the diaphragm 15. The apex angle 23 preferably equals or at least approximates the angle 23a enclosed by two divergent radiation beams which are made parallel by the optical elements 12 of the eyepiece 8. In the illustrated embodiment, the angle 23 equals or approximates 20°; the magnitude of this angle determines the deviation tolerance of an eye 10 in the position of FIG. 2.

In order to uniformly illuminate the entire observable area or field around the optical axis 9 in front of the eye 10, the perimeter 1 further comprises a partially transmitting mirror 24 which is inclined toward the plane 11 and crosses the optical axis 17. The mirror 17 transmits light which issues from the radiation source 13 and passes first through the aperture of the diaphragm 15 and thereupon through the collector lenses 16. At the same time, the mirror 24 directs light from a light source 25 toward the field lens 18 of the eyepiece 8. In order to further enhance the uniformity of illumination of the area or field around the optical axis 9, the perimeter 1 comprises a disc-shaped or otherwise configurated diffusor 26 which is installed between the light source 25 and the mirror 24. A collector lens 27 (e.g., a Fresnel lens) can be installed between the diffusor 26 and the mirror 24. The diffusor 26 can serve as a color filter if the apparatus of FIG. 2 is used for color perimetry.

In order to facilitate orientation of the eye 10 relative to the eyepiece 8, the perimeter 1 further comprises means for providing a brightly illuminated reference point or fixation mark. Such means includes a partly transmitting mirror 28 which crosses the axis 9 and is installed between the plane 11 and the optical elements 12 to transmit light which passes through the field lens 18 of the eyepiece 8 as well as to deflect light which is emitted from a further source 31. The mirror 28 directs such deflected light toward the eye 10 in the position of FIG. 2. The point of intersection of the mirror 28 by the axis 9 is further intersected by the common optical axis 29 of two optical elements 30 (e.g., lenses) in the path of propagation of light from the source 31 toward the mirror 28. The axis of the light source 31 coincides with the optical axis 29, and the means for presenting a reference point or fixation mark further comprises an apertured diaphragm 32 which is installed between the source 31 and the optical elements 30. The diaphragm 32 determines the area or size and the shape of the reference point.

A partially transmitting mirror 33 is installed between the optical elements 30 and the mirror 28 to cross the optical axis 29. The mirror 33 transmits visible light but reflects infrared light toward the infrared light sensitive CCD camera 34. The latter renders it possible to observe the eye 10 in the course of an examination. One, two or more sources 35 of infrared light are provided to illuminate the eye 10 in the course of an examination. The eye 10 does not discern the light which is emitted by the source or sources 35 but such radiation enables the camera to permit "secret" visual observation of the eye 10 in the course of a perimetric examination. The camera 34 is designed to transmit to the computer 2 signals constituting or imitating the image of the pupil of the eye 10 in the position of FIG. 2. This enables the computer 2 to ascertain that the subject who is being examined has detected or perceived a stimulus because the pupil has been altered as a result of such detection. Thus, and as already mentioned above, the computer 2 can receive (from the camera 34) objective signals in addition to or in lieu of signals which are transmitted in response to actuation of the patient-controlled knob 7.

FIG. 2 further shows the sensor 36 which serves to monitor the brain waves or changes of potential in another part or organ of the patient's body in order to ensure that the computer 2 can receive objective signals in addition to or in lieu of those transmitted by the knob 7. The sensor 36 transmits a signal when the patient perceives a stimulus, i.e., the mode of operation of the sensor 36 is analogous to that of the camera 34.

The collector lenses 16 and the field lens 18 can be omitted if the radiation source 13 and the diaphragm 15 are moved so close to the eyepiece 8 that the plane 19 of the diaphragm 15 coincides with the plane 11. This can be realized by placing a screen (not shown) into the plane 11. If such screen is placed into the plane 11 to present stimuli to the eye 10 while the eye assumes the position of FIG. 2, the stimuli can be selected in such a way that they are darker than the surroundings.

In either of the above described embodiments, the distance of the eye 10 from the plane 11 of real images of the stimuli is less than the sharp visual range or distance.

An important advantage of the improved method and apparatus is that the examination can be completed within a minute fraction of the heretofore required time. This is due to the fact that the tests need not be repeated, i.e., once the computer 2 has selected a particular location, the perimeter 1 presents to the eye a stimulus whose value increases until the stimulus is detected or discerned by the eye and such detection is signalled to the computer 2 via knob 7 and/or camera 34 and/or sensor 36. If desired, particularly for the purposes of reviewing the correctness of the examination, the person in charge may wish to carry out a second set of tests by presenting the eye 10 with stimuli of different value at some or all of the previously selected locations.

The exact manner in which the computer 2 can control the size of the aperture of the diaphragm 15 and/or the intensity of radiation issuing from the source 13 is well known and need not be described here.

The apparatus can be equipped only with the knob 7 or an equivalent device. However, it is often preferred to additionally equip the apparatus with the camera 34 and/or with the sensor 36 in order to ensure predictable transmission of signals to the computer 2 when the subject is incapable of actuating or is unwilling to actuate the knob 7.

The information pertaining to the locations of application of successive stimuli in the area of the optical axis can be stored in the internal memory of the computer 2 and/or in the external memory 3.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of examining the field of vision of a subject's eye with a computer-controlled perimeter, comprising the steps of locating the eye at, or at least close to, a predetermined position in which the optical axis of the eye is maintained in, or at least close to, a predetermined orientation; presenting to the eye at said position a sequence of stimuli from a source of radiaiton and substantially only once at each of a plurality of computer-selected locations is the area of the optical axis of the eye; increasing the value of each stimulus until the eye discerns the presented stimulus and the subject reacts as a result of discernment of the presented stimulus; generating signals denoting that value of each stimulus which is discerned by the eye at said position; transmitting said signals to the computer; and terminating the presentation of a stimulus in response to transmission of the corresponding signal to the computer.

2. The method of claim 1, wherein said step of increasing the value of each stimulus includes continuously increasing said value.

3. The method of claim 1, wherein said step of increasing the value of each stimulus includes increasing said value in a plurality of stages.

4. The method of claim 1, wherein said step of increasing the value of each stimulus includes increasing the intensity of radiation from the source.

5. The method of claim 1, wherein said step of increasing the value of each stimulus includes increasing the size of the stimulus.

6. The method of claim 1, wherein said signal generating step includes subjective generation of signals by the subject.

7. The method of claim 6, wherein said subjective generation includes actuation by the subject of a signal generating knob upon discernment of a stimulus.

8. The method of claim 1, wherein said signal generating step includes objective generation of signals by the subject.

9. The method of claim 8, wherein said objective generation includes monitoring the pupil of the eye at said position and generating signals in response to those changes of the pupil which are indicative of discernment of stimuli by the eye.

10. The method of claim 9, wherein said monitoring step includes observing the eye at said location with an infrared light sensitive CCD camera.

11. The method of claim 8, wherein said objective generation includes monitoring a part of the subject other than the eye at said position for changes of voltage is a result of increasing value of stimuli and generating signals in response to detection of voltages which are indicative of discernment of the respective stimuli by the eye at said position.

12. The method of claim 11, wherein said monitoring includes monitoring the brain of the subject for changes of brain waves.

13. Apparatus for examining the field of vision of a subject's eye, comprising a perimeter having means for locating the eye at, or at least close to, a predetermined position in which the optical axis of the eye is maintained in, or at least close to, a predetermined orientation, a source of radiation, and means for presenting stimuli to the eye from said source; and further including means for increasing the value of said stimuli, and means for generating value signals denoting the value of each stimuli discerned by the eye; means for transmitting said signals to a computer; and computer means for generating termination signals to terminate the presentation of a stimuli in response to discernment of such stimuli by the eye at said position.

14. The apparatus of claim 13, wherein said presenting means includes means for presenting stimuli of continuously increasing value.

15. The apparatus of claim 13, wherein said presenting means includes means for presenting stimuli of a value which increases in a plurality of stages.

16. The apparatus of claim 13, wherein said signal transmitting means includes subject-operated signal transmitting means.

17. The apparatus of claim 13, wherein said presenting means presents only a single stimuli at one location in the area of the optical axis of the eye.

* * * * *

UNITED STATES PATENT AND TRADEMARK OFFICE
CERTIFICATE OF CORRECTION

PATENT NO. : 5,319,398

DATED : June 7, 1994

INVENTOR(S) : Albert WEIJLAND

It is certified that error appears in the above-identified patent and that said Letters Patent is hereby corrected as shown below:

Column 9, Claim 1, line 43, "radiaiton" should read --radiation--;

line 45, "is" should read --in--.

Signed and Sealed this

Sixth Day of September, 1994

Attest:

BRUCE LEHMAN

Attesting Officer

Commissioner of Patents and Trademarks